United States Patent

Weber

[11] 3,959,340
[45] May 25, 1976

[54] CYANO-DISTYRYLBENZENES
[75] Inventor: Kurt Weber, Basel, Switzerland
[73] Assignee: Ciba-Geigy AG, Basel, Switzerland
[22] Filed: June 10, 1974
[21] Appl. No.: 477,947

Related U.S. Application Data
[62] Division of Ser. No. 42,598, June 1, 1970, Pat. No. 3,849,485.

[30] Foreign Application Priority Data
June 5, 1969 Switzerland.......................... 8652/69

[52] U.S. Cl............................ 260/465 K; 8/115.5; 8/116 R; 8/192; 260/465 F; 260/465 G; 260/507 R; 260/512 R; 252/301.16
[51] Int. Cl.²........................................ C07C 121/60
[58] Field of Search ......... 260/465 K, 465 G, 465 F

[56] References Cited
UNITED STATES PATENTS
3,822,305  7/1974  Pintschovius et al............... 260/465

Primary Examiner—Lewis Gotts
Assistant Examiner—Dolph H. Torrence
Attorney, Agent, or Firm—Joseph G. Kolodny; Edward McC. Roberts; Prabodh I. Almaula

[57] ABSTRACT
The invention concerns new asymetrical distyrylbenzenes and a process for their preparation, these compounds having the formula

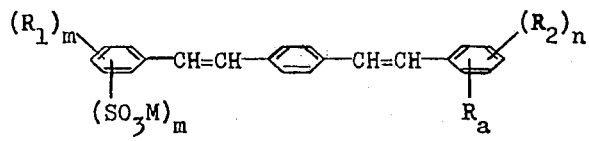

wherein $R_1$ and $R_2$ can be identical or different from one another and denote hydrogen, chlorine or fluorine, lower alkyl or lower alkoxy groups, $R_a$ represents hydrogen, the nitrile group or a carboxyl group, its salts, esters or amides, M denotes a hydrogen, alkali, alkaline earth, ammonium or amine salt ion, $m$ denotes the numbers 1 or 2 and $n$ denotes the numbers 1, 2 or 3, with the proviso that I. at least one of the substituents $R_1$, $R_2$ and $R_a$ is different from hydrogen and II. in the case where $R_a$ is different from hydrogen, $R_2$ represents hydrogen.

The new compounds are valuable optical brightening agents, especially in combination with detergents.

5 Claims, No Drawings

CYANO-DISTYRYLBENZENES

This is a division of application Ser. No. 42,598, filed on June 1, 1970 now U.S. Pat. No. 3,849,485, issued Nov. 19, 1974.

The present invention relates to new asymmetrically substituted monosulphonic acid derivatives of 1,4-distyrylbenzene, their manufacture and use as optical brighteners for organic materials.

A substantial number of derivatives of 1,4-distyrylbenzene have already been described, but these in general display a symmetric structure relative to the central phenylene group.

It has also already been pointed out that compounds of this type can be used as optical brighteners because of their fluoroescence behaviour.

It has now been found that amongst this general type of compound that is a specific narrowly limited group of compounds which is distinguished by conspicuously advantageous optical brightening properties, in comparison to similar or related compounds. This new group of compounds corresponds to the general formula

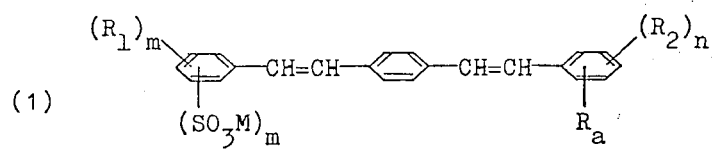

wherein $R_1$ and $R_2$ can be identical or different from one another and denote hydrogen, chlorine or fluorine, lower alkyl or lower alkoxy groups, $R_a$ represents hydrogen, the nitrile group or a carboxyl group, its salts, esters or amides, M denotes a hydrogen, alkali, alkaline earth, ammonium or amine salt ion, m denotes the numbers 1 or 2 and n denotes the numbers 1, 2 or 3, with the proviso that I. at least one of the substituents $R_1$, $R_2$ and $R_a$ is different from hydrogen and II. in the case where $R_a$ is different from hydrogen, $R_2$ represents hydrogen.

From the point of view of practical interest, the following sub-groups of compounds according to formula (1) should be mentioned:

a. Compounds which correspond to the formula

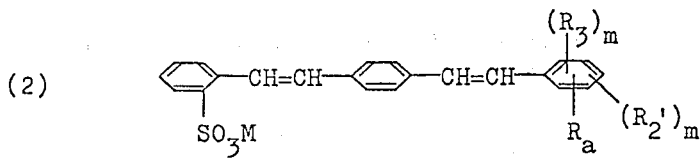

wherein $R_a$ represents hydrogen, a nitrile group located in positions 2 or 3 or a carboxyl group, its salts, esters or amides, $R_2'$ denotes hydrogen, chlorine, fluorine or an alkyl group containing 1 to 4 carbon atoms, $R_3$ denotes hydrogen or an alkoxy group located in positions 2 and/or 3, with 1 to 4 carbon atoms, M denotes a hydrogen, alkali, alkaline earth, ammonium or amine salt ion and m denotes the numbers 1 or 2, with the proviso that 1. at least one of the substituents is different from hydrogen, 2. in the case where $R_a$ is different from hydrogen, the symbols $R_2'$ and $R_3$ represent hydrogen, and 3. the total number of the substituents which are different from hydrogen is not more than 3.

b. Compounds of formula

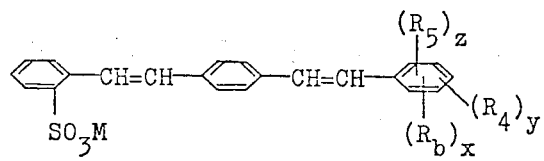

wherein $R_b$ denotes a nitrile group located in positions 2 or 3, $R_4$ denotes chlorine or an alkyl group containing 1 to 4 carbon atoms, $R_5$ denotes an alkoxy group located in position 2 and/or 3, with 1 to 4 carbon atoms, x represents 0 or 1, y represents 0, 1 or 2 and z represents 0, 1 or 2, with the sum of these index numbers having to fulfil one of the two conditions $$x + y + z = 1$$

and $$y + z = 2,$$

and wherein M represents a hydrogen, alkali, alkaline earth, ammonium or amine salt ion. The condition $(y + z) = 2$ is here to be understood in the sense that $x = 0$ at the same time.

c. Within the framework of the above formula, compounds of outstanding importance are those with a low number of carbon atoms in the substituents, that is to say compounds of formula

wherein $R_b$ denotes a nitrile group located in positions 2 or 3, $R_6$ denotes chlorine or a methyl group, and $R_7$ denotes a methoxy group located in positions 2 and/or 3, whilst in other respects the conditions given under formula (3) apply to x, y, z, and M.

In the compounds according to the above formulae (3) or (4) those types are preferred in cases of di-substitution by $R_4$ and/or $R_5$, or $R_6$ and/or $R_7$, in which at most one of the ortho-positions (relative to bonding of the R-substituted phenyl nucleus to the remaining molecule) is occupied.

Finally, compounds of the following formulae are of particular applicational interest:

(5) 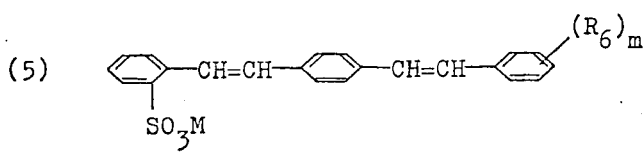

(6) 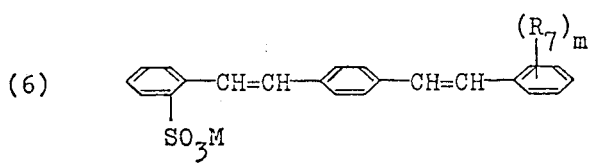

(7) 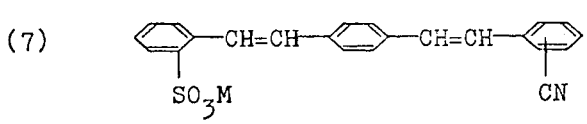

In these formulae $R_6$ denotes chlorine or a methyl group, $R_7$ denotes a methoxy group, m denotes the numbers 1 or 2 and M denotes a hydrogen, alkali, alkaline earth, ammonium or amine salt ion.

The distyrylbenzene derivatives of formula (1) and of the subordinate formulae can be manufactured analogously to methods which are in themselves known. In general, the procedure followed is that about 1 mol equivalent of a compound of formula (8) 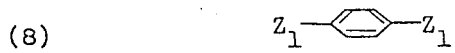

is reacted with about 1 mol equivalent of a compound of formula (9) 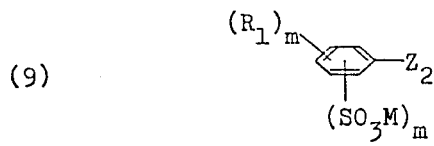

and about 1 mol equivalent of a compound of formula

(10) 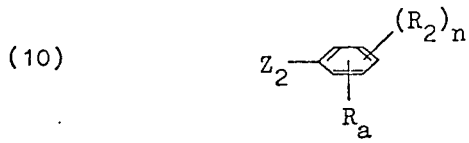

wherein M, $R_1$, $R_2$, $R_a$, m and n have the abovementioned significance, and one of the symbols $Z_1$ and $Z_2$ denotes a -CHO group and the other denotes one of the groupings of formulae

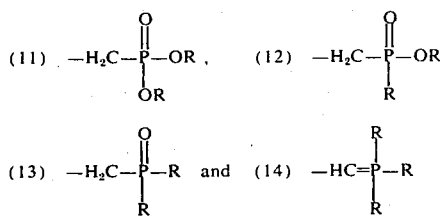

wherein R represents an optionally further-substituted alkyl radical, aryl radical, cycloalkyl radical or aralkyl radical, with the end product according to the formula given initially being isolated from the reaction mixture on the basis of its solubility in water.

Compounds of formula (2) can be manufactured quite analogously if about 1 mol equivalent of a compound of formula (8) 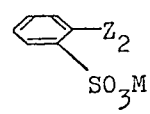

is reacted in the same manner with about 1 mol equivalent of a compound of formula

(15) 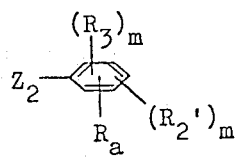

and about 1 mol equivalent of a compound of formula

(16) 

wherein M, $R_2'$, $R_3$, $R_a$ and m have the abovementioned significance.

Compounds of formula (3) are obtained quite analogously if about 1 mol equivalent of a compound of formula (8) 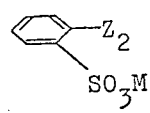

is reacted with about 1 mol equivalent of a compound of formula

(17) 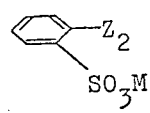

and about 1 mol equivalent of a compound of formula

(18) 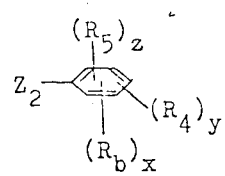

or if about 1 mol equivalent of a compound of formula

(19) 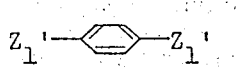

is reacted with about one mol equivalent of a compound of formula

(20) 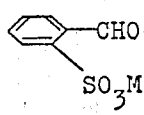

and about 1 mol equivalent of a compound of formula

(21) 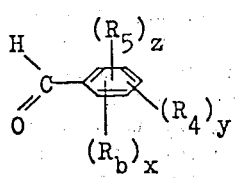

with the reaction conditions given above being observed.

Accordingly, it is thus for example possible to react terephthalaldehyde

(22) 

with monofunctional compounds of formulae

(23) 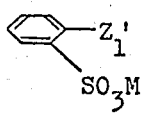

and (24) 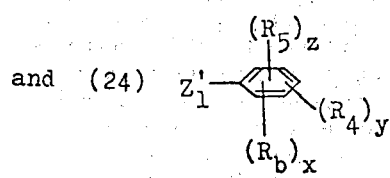

or monoaldehydes of formulae (20) and (21) with bifunctional compounds of formula

(25) 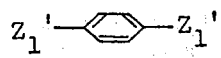

wherein M, $R_b$, $R_4$, $R_5$, $x$, $y$, and $z$ have the indicated significance and $Z_1'$ denotes one of the phosphorus-containing substituents of formulae (11), (12), (13) or (14).

The phosphorus compounds of formulae (23), (24) and (25) here required as starting substances are obtained in a manner which is in itself known by reacting halogenomethyl compounds, preferably chloromethyl or bromomethyl compounds of formula

(26) 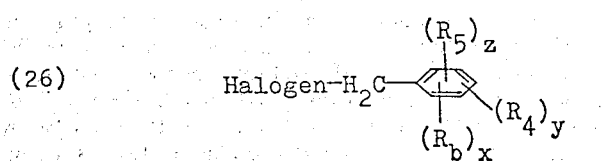

(27) 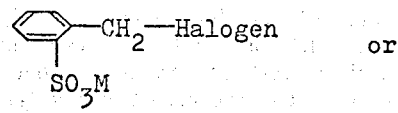 or

(28) 

with phosphorus compounds of formulae

(29) 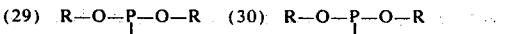 (30) 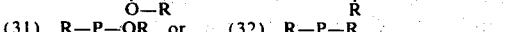

(31) 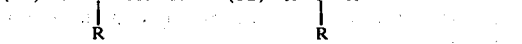 or (32) R—P—R
                                              |
                                              R In these formulae, R has the indicated significance, with radicals R bonded to oxygen preferably being lower alkyl groups, whilst radicals R directly bonded to phosphorus are preferably aryl radicals such as benzene radicals. The phosphorus compounds of formula (13) can also be obtained by reaction of halogenomethyl compounds, preferably chloromethyl or bromomethyl compounds of formulae (26), (27) or (28), with p-chlorodiphenylphosphine and subsequent reaction with an aLcohol of formula R-OH (significance of R as defined above), for example with methanol or with water.

A variant of particular practical importance consists of using, as phenylene components according to formulae (8), those corresponding to the formula

(33) 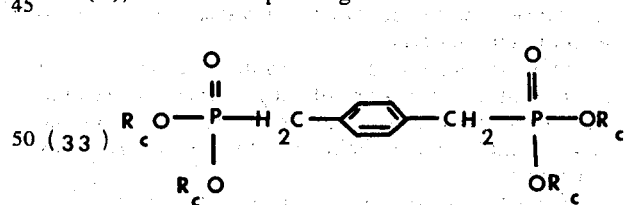

wherein $R_c$ denotes an alkyl group with 1 to 6 carbon atoms.

The manufacturing process is advantageously carried out in inert solvents. As examples thereof, hydrocarbons such as toluene and xylene or alcohols, such as methanol, ethanol, isopropanol, butanol, glycols, glycol-ethers such as 2-methoxyethanol, hexanols, cyclohexanol and cyclooctanol, and also ethers such as diisopropyl ether, tetrahydrofurane and dioxane as well as dimethylsulphoxide, formamide and N-methylpyrrolidone may be mentioned. Polar organic solvents such as dimethylformamide and dimethylsulphoxide are particularly suitable. Some of the reactions can also be carried out in aqueous solution.

The temperature at which the reaction is carried out can vary within wide limits. It is determined α) by the stability of the solvents used towards the reagents, especially towards the strongly basic alkali compounds β) by the reactivity of the condensation partners and γ) by the activity of the solvent-base combination as a condensation agent.

In practice, accordingly, temperatures between about 10° and 100°C can in general be used, especially if dimethylformamide or dimethylsulphoxide are used as the solvent. The preferred temperature range is 20° to 60°C. Under certain circumstances higher temperatures can however also be used if this is desirable for reasons of timesaving or it is intended to use a less active but on the other hand cheaper condensation agent. In principle, reaction temperatures in the range of 10° to 180°C are hence also possible.

Possible strongly basic alkali compounds are above all the hydroxides, amides and alcoholates (preferably those of primary alcohols containing 1 to 4 carbon atoms) of the alkali metals, and for economic reasons those of lithium, sodium and potassium are of predominant interest. In principle and in special cases it is however also possible successfully to use alkali sulphides and carbonates, aryl-alkali compounds such as for example phenyllithium, or strongly basic amines (including ammonium bases, for example dialkylammonium hydroxides).

Because of competing reaction of the three reagents, the process described above in the first instance mostly yields mixtures of asymmetrically substituted distyrylbenzene derivatives according to formula (1) and the two corresponding symmetrically substituted distyrylbenzene derivatives. The separation of these components cna be effected, on the basis of their different solution behaviour, in water, by separating off the water-insoluble compound by filtration. The water-soluble compounds which remain in the filtrate can then be separated on the basis of their differing solubility in water.

The new compounds defined above show a more or less pronounced fluorescence in the dissolved or finely divided state. They can be used for the optical brightening of the most diverse synthetic, semi-synthetic or natural organic materials or substances which contain such organic materials.

The following groups of organic materials, to the extent that an optical brightening of these is relevant, may be mentioned as examples thereof, without the survey which follows being intended to express any restriction:

I. Synthetic organic high molecular materials:
  a. Polymerisation products based on organic compounds containing at least one polymerisable carbon-carbon double bond, that is to say their homopolymers and copolymers as well as their after-treatment products such as for example crosslinking, grafting or degradation products, polymer dilutions or products obtained by modification of reactive groups, for example polymers based on α,β-unsaturated carboxylic acids or derivatives of such carboxylic acids, especially on acrylic compounds (such as for example acrylic esters, acrylic acid, acrylonitrile, acrylamides and their derivatives or their methacrylic analogues), on olefine hydrocarbons (such as for example ethylene, propylene, styrenes or dienes, and also socalled ABS polymers), and polymers based on vinyl and vinylidene compounds (such as for example vinyl chloride, vinyl alcohol and vinylidene chloride),
  b. polymerisation products which are obtainable by ring opening, for example polyamides of the polycaprolactam type, and also polymers which are obtainable both via polyaddition and polycondensation, such as polyethers or polyacetals,
  c. polycondensation products or precondensates based on bifunctional or polyfunctional compounds possessing condensable groups, their homocondensation and cocondensation products as well as products of after-treatment, such as for example polyesters, especially saturated (for example ethylene glycol-terephthalic acid polyesters) or unsaturated (for example maleic acid-dialcohol polycondensates as well as their crosslinking products with copolymerisable vinyl monomers), unbranched as well as branched polyesters (also those based on higherfunctional alcohols, such as for example alkyd resins), polyamides (for example hexamethylenediamine adipate), maleate resins, melamine resins, their precondensates and analogues, polycarbonates and silicones,
  d. polyaddition products such as polyurethanes (crosslinked and not crosslinked) and epoxide resins.

II. Semi-synthetic organic materials, for example cellulose esters of different degrees of esterification (so-called 2½-acetate and triacetate) or cellulose ethers, regenerated cellulose (viscose and cuprammonium cellulose) or their after-treatment products, and casein plastics.

III. Natural organic materials of animal or vegetable origin, for example based on cellulose or proteins such as cotton, wool, linen, silk, natural lacquer resins, starch and casein.

The organic materials to be optically brightened can belong to the most diverse processing states (raw materials, semi--finished goods or finished goods). They can on the other hand be in the form of the most diverse shaped structures, that is to say for example in the form of predominantly three-dimensional bodies such as sheets, profiles, injection mouldings, various machined articles, chips, granules or foams, and also as predominantly two-dimensional bodies such as films, foils, lacquers, coatings, impregnations and coverings, or as predominantly one-dimensional bodies such as filaments, fibres, flocks and wires. The said materials can, on the other hand, also be in unshaped states, in the most diverse homogeneous or inhomogeneous forms of division, such as for example as powders, solutions, emulsions, dispersions, latices, pastes or waxes.

Fibre materials can for example be in the form of endless filaments (stretched or unstretched), staple fibres, flocks, hanks, textile filaments, yarns, threads, fibre fleeces, felts, waddings, flocked structures or woven textile fabrics or textile laminates, knitted fabrics as well as papers, cardboards or paper compositions.

The compounds to be used according to the invention are, inter alia, of importance for the treatment of textile organic materials, especially woven textile fabrics. To the extent that fibres, which can be in the form of staple fibres or endless filaments, and in the form of hanks, woven fabrics, knitted fabrics, fleeces, flocked substrates or laminates, are to be optically brightened according to the invention, this is advantageously done in an aqueous medium, with the compounds in question being in a finely divided form (suspensions, socalled micro-dispersions and, where appropriate solutions). If appropriate, dispersing agents, stabilisers, wetting agents and further auxiliary agents can be added during the treatment.

Depending on the type of brightener compound used, it can prove advantageous to carry out the process in a neutral or alkaline or acid bath. The treatment is usually carried out at temperatures of about 20° to 140°C, for example at the boil of the bath or near this (about 90°C). For the finishing of textile substrates according to the invention it is also possible to use solutions or emulsions in organic solvents, as is practised in the dyeing industry in so-called solvent dyeing (padder heatfixing application, or exhaustion dyeing process in dyeing machines).

The new optical brighteners according to the present invention can furthermore be added to, or incorporated into, the materials before or during their shaping. Thus they can for example be added to the compression moulding or injection moulding composition in the manufacture of films, foils for example milling into hot polyvinyl chloride) or mouldings.

Where fully synthetic or semi-synthetic organic materials are shaped by spinning processes or via spinning compositions, the optical brighteners can be applied in accordance with the following processes: addition to the starting substances (for example monomers) or intermediate products (for example precondensates or prepolymers), that is to say before or during the polymerisation, polycondensation or polyaddition, powdering onto polymer chips or granules for spinning compositions, bath dyeing of polymer chips or granules for spinning compositions, metered addition to spinning melts or spinning solutions, or application to spinning tow before stretching.

The new optical brighteners according to the present invention can for example also be employed in the following use forms:

a. Mixtures with dyestuffs (shading) or pigments (coloured pigments or especially, for example white pigments) or as an additive to dyebaths, printing pastes, discharge pastes or reserve pastes. Furthermore also for the aftertreatment of dyeings, prints or discharge prints, b. mixed with so-called "carriers," wetting agents, plasticisers, swelling agents, antioxidants, light protection agents, heat stabilisers and chemical bleaching agents (chlorite bleach and bleaching bath additives), c. in a mixture with crosslinking agents and finishing agents (for example starch or synthetic finishing agents), and also in combination with the most diverse textile finishing processes, especially synthetic resin finishes (for example creaseproof finishes such as "wash-and-wear", "permanent-press" and "no-iron"), and also flameproofing, soft handle, "anti-soiling" or antistatic finishes or antimicrobial finishes, d. incorporation of the optical brighteners into polymeric carrier materials (polymerisation, polycondensation or polyaddition products) in a dissolved or dispersed form, for use in, for example, coating agents, impregnating agents or adhesives (solutions, dispersions or emulsions) for textiles, fleeces, paper or leather, e. as additives to co-called "master batches,"

f. as additives to the most diverse industrial products, in order to render these more marketable (for example improvement of the appearance of soaps, detergents and pigments), g. in combination with other optically brightening substances, h. in spinning bath preparations, that is to say as additives to spinning baths, such as are used to improve the slip for the further processing of synthetic fibres, or from a special bath before the esterification of the fibre, and i. as scintillators, for various purposes of a photographic nature, such as for example for electrophotographic reproduction or super-sensitisation.

If the brightening process is combined with textile treatment or finishing methods, the combined treatment can in many cases advantageously be carried out with the aid of appropriate stable preparations which contain the optically brightening compounds in such concentration that the desired brightening effect is achieved.

In certain cases the brighteners are rendered fully effective by an after-treatment. This can for example represent a chemical treatment (for example acid treatment), a heat treatment (for example heat) or a combined chemical/heat treatment. Thus an appropriate procedure to follow when optically brightening a series of fibre substrates, for example of polyester fibres, with the brighteners according to the invention is, for example, to impregnate these fibres with the aqueous dispersions (optionally also solutions) of the brighteners at temperatures below 75°C, for example at room temperature, and to subject them to a dry heat treatment at temperatures above 100°C, it being generally advisable first still to dry the fibre material at a moderately elevated temperature, for example at not less than 60° up to about 130°C. The heat treatment in the dry state is then advantageously carried out at temperatures between 120° and 225°C, for example by heating in a drying chamber, by ironing in the stated temperature range or also by treatment with dry superheated steam. The drying and the dry heat treatment can also be carried out in immediate succession or be combined into a single process step.

The amount of the new optical brighteners to be used according to the invention, relative to the material to be optically brightened, can vary within wide limits. A distinct and durable effect can already be achieved with very small amounts, in certain cases for example amounts of 0.0001 percent by weight. However, amounts of up to about 0.8 percent by weight and in certain cases up to about 2 percent by weight can also be employed. For most practical purposes amounts of between 0.0005 and 0.5 percent by weight are of preferential interest.

The new optical brighteners are also particularly suitable for use as additives to washing baths or to commercial or domestic detergents, and can be added in various ways. In the case of washing baths they are appropriately added in the form of their solutions in water or organic solvents or also in a finely divided form as aqueous dispersions. They are advantageously added to domestic or commercial detergents in any stage of the process of manufacture of the detergents, for example to the so-called "slurry" before the spray-drying of the detergent powder, or during the preparation of liquid detergent combinations. The addition can be made both in the form of a solution or dispersion in water or other solvents and without an auxiliary agent, as a dry brightener powder. The brighteners can for example be mixed, kneaded or ground with the detergent substances and mixed into the finished washing powder in this way. They can however also be sprayed, in a dissolved or pre-dispersed form, onto the finished detergent.

Possible detergents are the known mixtures of detergent substances such as for example soap in the form of chips and powder, synthetics, soluble salts of sulphonic acid half-esters of higher fatty alcohols, higher and/or multiply alkyl-substituted arylsulphonic acids, sulphocarboxylic acid esters of medium to higher alcohols, fatty acid acylaminoalkyl- or -aminoaryl- glycerinesulphonates, phosphoric acid esters of fatty alcohols and the like. Possible so-called "builders" are, for example, alkali polyphosphates and polymetaphosphates, alkalipyrophosphates, alkali salts of carboxymethylcellulose and other "soil redeposition inhibitors", and also alkali silicates, alkali carbonates, alkali borates, alkali perborates, nitrilotriacetic acid, ethylenediaminotetraacetic acid, and foam stabilisers such as alkanolamides of higher fatty acids. Furthermore, the detergents can for example contain: antistatic agents, fat-restoring skin protection agents such as lanolin, enzymes, anti-microbial agents, perfumes and dyestuffs.

The new optical brighteners have the particular advantage that they are also effective in the presence of active chlorine donors, such as for example hypochlorite, and can be used without significant loss of the effects in wash baths containing non-ionic detergents, for example alkylphenol-polyglycol-ethers.

The compounds according to the invention are added in amounts of 0.005 – 1% or above, relative to the weight of the liquid or pulverulent finished detergent. Washing liquors which contain the stated amounts of the optical brighteners claimed impart a brilliant appearance in daylight when washing textiles of cellulose fibres, polyamide fibres, cellulose fibres with a high quality finish, polyester fibres, wool and the like.

The washing treatment is for example carried out as follows:

The textiles mentioned are treated for 1 to 30 minutes, at 20° to 100°C, in a washing bath which contains 1 to 10 g/kg of a built-up composite detergent and 0.05 to 1%, relative to the weight of the detergent, of the brighteners claimed. The liquor ratio can be 1:3 to 1:50. After washing, the material is rinsed and dried in the usual manner. The washing bath can contain 0.2 g/l of active chlorine (for example as hypochlorite) or 0.1 to 2 g/l of sodium perborate as a bleaching additive.

Within the framework of the present invention it is also directly possible — depending on the special technical use requirements — to employ the new compounds described mixed with the corresponding compounds of symmetrical structure, obtainable from the competing reaction of the manufacturing process, for the purpose of optical brightening. This means that in applicational practice a separation of the competing reaction products can also be dispensed with, depending on the end use. In certain cases, the symmetrical water-insoluble compound can be separated off, whilst the water-soluble compounds are employed as a mixture for the purpose of optical brightening.

In the examples the parts, unless otherwise stated, are always parts by weight and the percentages are always percentages by weight. Unless otherwise noted, melting points and boiling points are uncorrected.

EXAMPLE 1.

A mixture of 18.9 g of 1,4-bis-(diethoxyphosphonomethyl)-benzene, 6.8 g of 2-methoxybenzaldehyde and 10.5 g of the sodium salt of benzaldehyde-2-sulphonic acid (about 98% strength) is introduced into a well-stirred suspension of 24.5 g of potassium hydroxide powder (about 91% strength) in 200 ml of anhydrous dimethylformamide after displacing the air by nitrogen, and in the course of the addition the temperature rises to about 40°C. The mixture is then stirred for a further 2 hours at 40° to 45°C. The reaction mixture is poured onto 1.5 liters of distilled water at about 70°C, about 500 g of ice are then added, the pH-value of the solution is adjusted to about 7 by adding 37% strength hydrochloric acid, and the product which has crystallised out is filtered off, washed with an approximately 17% strength sodium chloride solution and dried in vacuo at about 100°C.

The product is boiled up in 500 ml of dimethylformamide and clarified by filtration, and the clear solution is mixed with 100 ml of distilled water, cooled and again clarified by filtration. 2.2 liters of distilled water are added to the filtrate, the mixture is heated to 50°C, 46 g of sodium chloride are added, the whole is cooled, and the product which has crystallised out is filtered off and dried in vacuo at about 100°C.

Yield: 2.7 g of the potassium/sodium salt of the sulphonic acid of formula

(34) 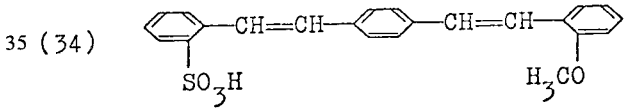

EXAMPLE 2.

The procedure described in Example 1 is followed, but 49.2 g of potassium hydroxide powder (about 91% strength) in 200 ml of anhydrous dimethylformamide, and a mixture of 37.8 g of 1,4-bis-(diethoxyphosphonomethyl)benzene, 16.6 g of 2,3-dimethoxybenzaldehyde and 21.2 g of the sodium salt of benzaldehyde-2-sulphonic acid (about 98% strength) in 100 ml of anhydrous dimethylformamide are used. Working-up takes place as follows:

The reaction mixture is poured onto about 2 liters of distilled water at about 70°C, 300 g of sodium chloride and about 1 kg of ice are added, and the product which has crystallised out is filtered off and washed with about 17% strength sodium chloride solution. The filter cake is boiled up in 800 ml of distilled water and filtered through a pressure filter, the clear filtrate is cooled and the product which has crystallised out is filtered off. The filter cake is recrystallised from about 100 ml of ethanol and dried in vacuo at about 100°C.

Yield: 2.5 g of the potassium/sodium salt of the sulphonic acid of formula

(35) 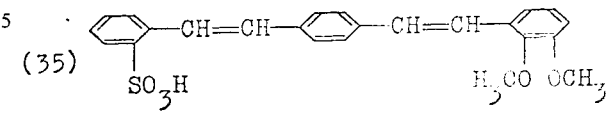

EXAMPLE 3.

The procedure described in Example 2 is followed, but instead of 16.6 g of 2,3-dimethoxybenzaldehyde, 14.0 g of p-chlorobenzaldehyde are used. The working-up of the crude reaction mixture takes place as follows:

The filter cake is boiled up in a mixture of 750 ml of distilled water and 750 ml of dimethylformamide, clarified by filtration through a pressure filter, and the clear filtrate mixed with 750 ml of distilled water and 75 g of sodium chloride and cooled. The product which has crystallised out is filtered off, recrystallised from about 600 ml of ethanol and dried in vacuo at about 100°C. Yield: 3.3 g of the potassium/sodium salt of the sulphonic acid of formula (36)

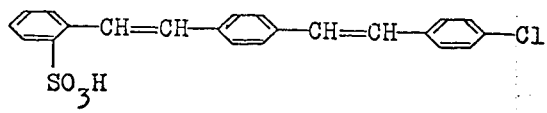

The compounds of formula

(37) 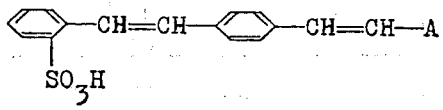

listed in the table which follows can be manufactured in the form of their sodium or potassium salts (in the form of light yellow powders) in a similar manner to that described in the preceding examples.

| No. | −A |
|---|---|
| 38 | ⌬−Cl with Cl |
| 39 | ⌬ with Cl |
| 40 | ⌬ with CH₃ |
| 41 | ⌬−CH₃ |
| 42 | ⌬ with CN |
| 43 | ⌬ with CN |
| 44 | ⌬ with COOCH₃ |
| 45 | ⌬ with F |
| 46 | ⌬ with Cl, Cl |

| No. | -A |
|---|---|
| 47 | 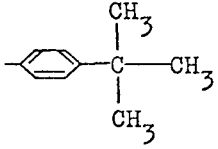 |
| 48 | 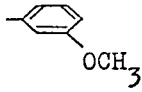 |
| 49 | 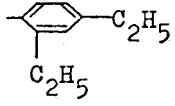 |
| 50 | 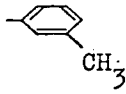 |
| 51 | 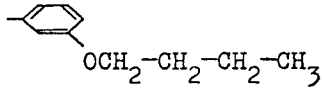 |
| 52 | 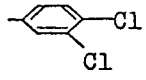 |
| 53 | 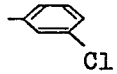 |

The corresponding sodium salts are obtained by using sodium methylate instead of potassium hydroxide powder. Equally, the equivalent amount of 1,4-bis-(dimethoxyphosphonomethyl)-benzene can be used instead of 1,4-bis(diethoxy-phosphonomethyl)-benzene. Finally, dimethylsulphoxide can also be used as a solvent instead of dimethylformamide.

EXAMPLE 4.

Bleached cotton fabric is washed for 15 minutes, using a liquor ratio of 1:20, in a liquor warmed to 50°C which contains the following additives per liter: 0.004 to 0.016 g of the brightener of formula (35), (36), (38), (39), (40) or (41), 0.25 g of active chlorine (Javelle solution), and 4 g of a washing powder of the following composition: 15.00% of dodecylbenzenesulphonate, 10.00% of sodium laurylsulphonate, 40.00% of sodium tripolyphosphate, 25.75% of anhydrous sodium sulphate, 7.00% of sodium metasilicate, 2.00% of carboxymethylcellulose and 0.24% of ethylenediaminetetraacetic acid. The cotton fabric is here only introduced into the bath 15 minutes after preparing the washing bath, warmed to 50°C. After rinsing and drying, the fabric shows a good brightening effect of good fastness to acid, light and chlorine.

A good brightening effect is also obtained, if the washing process is carried out in the same manner for 15 minutes at 25°C.

The washing powder of the abovementioned composition can also contain the brighteners of the formulae referred to above, directly incorporated.

EXAMPLE 5.

A polyamide fibre fabric (Perlon-Helanca) is washed for 15 minutes, using a liquor ratio of 1:20, in a liquor warmed to 50°C, which contains the following additives per liter: 0.004 to 0.016 g of the brightener of formulae (34), (35), (36), (38), (40) or (41), 0.25 g of active chlorine (Javelle solution), 4 g of a washing powder of the following composition: 15.00% of dodecylbenzenesulphonate, 10.00% of sodium laurylsulphonate, 40.00% of sodium tripolyphosphate, 25.75% of anhydrous sodium sulphate, 7.00% of sodium metasilicate, 2.00% of carboxymethylcellulose and 0.25. % of ethylenediaminetetraacetic acid. The polyamide fibre fabric is only introduced into the washing bath, warmed to 50°C, 15 minutes after its preparation. After rinsing and drying, the fabric shows a good brightening effect of good fastness to light.

A good brightening effect is also obtained if the washing process is carried out in the same manner, but at 25°C.

The washing powder of the abovementioned composition also contain the brighteners of the formulae referred to above, directly incorporated.

EXAMPLE 6.

A polyamide fibre fabric (Perlon) is introduced at 60°C, using a liquor ratio of 1:40, into a bath which (relative to the weight of the fabric) contains 0.1% of one of the brighteners of formulae (35), (36), (38), (40) or (41) and also 1 g of 80% strength acetic acid and 0.25 g of an addition product of 30 to 35 mols of ethylene oxide to one mol of technical stearyl alcohol, per liter. The mixture is warmed to the boil over the course of 30 minutes and kept at the boil for 30 minutes. After rinsing and drying, a good brightening effect is achieved.

If instead of the polyamide-6 fabric a polyamide-66 (nylon) fabric is used, similar brightening effects are obtained.

Finally, it is also possible to work under high temperature conditions, for example for 30 minutes at 130°C. For this type of use, it is advisable to add 3 g/l of hydrosulphite to the liquor.

EXAMPLE 7.

10,000 g of a polyamide, manufactured from hexamethylenediamine adipate in a known manner, in chip form, are mixed for 12 hours in a tumbler vessel with 30 g of titanium dioxide (rutile modification) and 5 g of one of the compounds of formulae (34), (35), (36), (38), (39), (40) or (41). The chips treated in this way are fused in a kettle heated to 300°–310°C by means of oil or diphenyl vapour, after displacing the atmospheric oxygen by steam, and are stirred for half an hour. The melt is thereafter extruded through a spinning die under a nitrogen pressure of 5 atmospheres gauge and the cooled filament spun in this way is wound up on a spinning bobbin. The resulting filaments show a good brightening effect.

If instead of a polyamide manufactured from hexamethylenediamine adipate a polyamide manufactured from ε-caprolactam is used, similar good results are obtained.

EXAMPLE 8.

A cotton fabric article provided with a non-iron finish by means of an aminoplastic resin is washed for 15 minutes, using a liquor ratio of 1:20, in a liquor warmed to 50°C which contains the following additives per liter: 0.004 to 0.016 g of a brightener of formulae (34), (35), (36), (38), (40) or (41), and 4 g of a washing powder of the following composition: 15.00% of dodecylbenzenesulphonate, 10.00% of sodium laurylsulphonate, 40.00% of sodium tripolyphosphate, 25.75% of anhydrous sodium sulphate, 7.00% of sodium metasilicate, 2.00% of carboxymethylcellulose and 0.25% of ethylenediaminetetraacetic acid. After rinsing and drying, the fabric displays a higher white content in daylight than does the untreated material.

I claim:

1. Di-styrylbenzene derivatives of the formula $$\text{[structure with } SO_3M, CH=CH, (R_3)_m, R_a, (R_2')_m \text{]}$$

wherein $R_a$ represents a nitrile group located in positions 2 or 3, $R_2'$ denotes hydrogen, chlorine, fluorine or an alkyl group containing 1 to 4 carbon atoms, $R_3$ denotes hydrogen or an alkoxy group located in positions 2 and/or 3, with 1 to 4 carbon atoms, M denotes a hydrogen, alkali, alkaline earth, ammonium or amine salt ion and m denotes the numbers 1 or 2, with the proviso that 1. at least one of the substituents is different from hydrogen, 2. in the case where $R_a$ is different from hydrogen, the symbols $R_2'$ and $R_3$ represent hydrogen, and 3. the total number of the substituents which are different from hydrogen is not more than 3.

2. Di-styrylbenzene derivatives according to claim 1, which correspond to the formula $$\text{[structure with } SO_3M, CH=CH, (R_5)_z, (R_b)_x, (R_4)_y \text{]}$$

wherein $R_b$ denotes a nitrile group located in positions 2 or 3, $R_4$ denotes chlorine or an alkyl group containing 1 to 4 carbon atoms, $R_5$ denotes an alkoxy group located in positions 2 and/or 3, with 1 to 4 carbon atoms, x represents 0 or 1, y represents 0, 1 or 2 and z represents 0, 1 or 2, with the sum of these index numbers having to fulfil one of the two conditions $$x + y + z = 1$$

and $$y + z = 2,$$

and wherein M represents a hydrogen, alkali, alkaline earth, ammonium or amine salt ion.

3. Di-styrylbenzene derivatives according to claim 1 which correspond to the formula $$\text{[structure with } SO_3M, CH=CH, (R_7)_z, (R_b)_x, (R_6)_y \text{]}$$

wherein $R_b$ denotes a nitrile group located in positions 2 or 3, $R_6$ denotes chlorine or methyl group, $R_7$ denotes a methoxy group located in positions 2 and/or 3, x represents 0 or 1, y represents 0, 1 or 2 and z represents 0, 1 or 2, with the sum of these index numbers having to fulfil one of the two conditions $$x + y + z = 1$$

and $$y + z = 2.$$

and wherein M represents a hydrogen, alkali, alkaline earth, ammonium or amine salt ion.

4. Di-styrylbenzene derivatives according to claim 1 which correspond to the formula

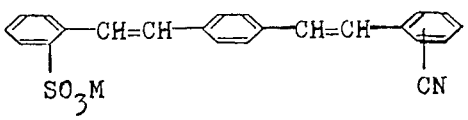

wherein the nitrile group is located in positions 2 or 3 and M represents a hydrogen, alkali, alkaline earth, ammonium or amine salt ion.

5. Di-styrylbenzene derivatives according to claim 2, which correspond to the formula

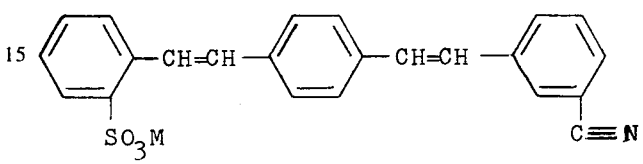

wherein M represents a hydrogen, alkali, alkaline earth, ammonium or amine salt ion.

* * * * *